United States Patent
Joseph et al.

(10) Patent No.: US 10,117,704 B2
(45) Date of Patent: Nov. 6, 2018

(54) ENERGY-ACTIVATION MECHANISMS FOR SURGICAL INSTRUMENTS

(71) Applicant: COVIDIEN LP, Mansfield, MA (US)

(72) Inventors: Daniel A. Joseph, Golden, CO (US); Gene H. Arts, Berthoud, CO (US); Tony Moua, Broomfield, CO (US)

(73) Assignee: COVIDIEN LP, Mansfield, MA (US)

( * ) Notice: Subject to any disclaimer, the term of this patent is extended or adjusted under 35 U.S.C. 154(b) by 552 days.

(21) Appl. No.: 14/799,853

(22) Filed: Jul. 15, 2015

(65) Prior Publication Data

US 2016/0058496 A1    Mar. 3, 2016

Related U.S. Application Data

(60) Provisional application No. 62/042,536, filed on Aug. 27, 2014.

(51) Int. Cl.
*A61B 18/14* (2006.01)
*A61B 18/00* (2006.01)

(52) U.S. Cl.
CPC ...... *A61B 18/1442* (2013.01); *A61B 18/1445* (2013.01); *A61B 18/1477* (2013.01);
(Continued)

(58) Field of Classification Search
CPC ........... A61B 2018/00934; A61B 2018/00172; A61B 2018/00916; A61B 2018/00922;
(Continued)

(56) References Cited

U.S. PATENT DOCUMENTS

| 1,813,902 A | 7/1931 | Bovie |
| 3,372,288 A | 3/1968 | Wigington |

(Continued)

FOREIGN PATENT DOCUMENTS

| CN | 201524137 U | 7/2010 |
| CN | 103118614 A | 5/2013 |

(Continued)

OTHER PUBLICATIONS

Extended European Search Report corresponding to counterpart Int'l Appln. No. EP 15 17 8229.9 dated Jan. 14, 2016.

(Continued)

*Primary Examiner* — Lee S Cohen
*Assistant Examiner* — Ryan T Clark

(57) ABSTRACT

A surgical instrument includes a housing, energizable member, first activation switch, cable assembly, and second activation switch. The housing is operatively associated with the energizable member. The first activation switch is coupled to the energizable member and is selectively transitionable from an open condition to a closed condition. The cable assembly is coupled to the housing at a first end and includes a plug at a second, opposite end, the plug housing a second activation switch selectively transitionable from an open condition to a closed condition. The plug is adapted to connect to the source of electrosurgical energy, wherein transitioning of the first activation switch from the open condition to the closed condition transitions the second activation switch from the open condition to the closed condition such that the second activation switch communicates with the source of electrosurgical energy to initiate the supply of energy to the energizable member.

18 Claims, 6 Drawing Sheets

(52) U.S. Cl.
CPC .. *A61B 18/1482* (2013.01); *A61B 2018/0094* (2013.01); *A61B 2018/00589* (2013.01); *A61B 2018/00595* (2013.01); *A61B 2018/00916* (2013.01); *A61B 2018/00922* (2013.01); *A61B 2018/00928* (2013.01); *A61B 2018/00934* (2013.01); *A61B 2018/00958* (2013.01); *A61B 2018/1467* (2013.01)

(58) Field of Classification Search
CPC .. A61B 2018/00928; A61B 2018/0094; A61B 2018/00958; A61B 1/00124
See application file for complete search history.

(56) References Cited

U.S. PATENT DOCUMENTS

| | | | |
|---|---|---|---|
| 4,112,950 | A | 9/1978 | Pike |
| 4,619,258 | A | 10/1986 | Pool |
| 4,655,215 | A | 4/1987 | Pike |
| 4,846,171 | A | 7/1989 | Kauphusman et al. |
| 5,313,027 | A | 5/1994 | Inoue et al. |
| 5,472,443 | A * | 12/1995 | Cordis .............. A61B 18/12 606/32 |
| 5,633,578 | A * | 5/1997 | Eggers ............ A61B 18/1206 323/301 |
| 6,074,386 | A | 6/2000 | Goble et al. |
| 6,325,795 | B1 | 12/2001 | Lindemann et al. |
| 6,616,658 | B2 | 9/2003 | Ineson |
| 6,652,514 | B2 | 11/2003 | Ellman et al. |
| 6,808,525 | B2 | 10/2004 | Latterell et al. |
| 6,934,134 | B2 | 8/2005 | Mori et al. |
| 6,966,907 | B2 | 11/2005 | Goble |
| 6,977,495 | B2 | 12/2005 | Donofrio |
| 6,979,786 | B2 | 12/2005 | Aukland et al. |
| 6,994,707 | B2 | 2/2006 | Ellman et al. |
| 7,145,757 | B2 | 12/2006 | Shea et al. |
| 7,416,437 | B2 | 8/2008 | Sartor et al. |
| 7,837,685 | B2 | 11/2010 | Weinberg et al. |
| 9,433,460 | B2 * | 9/2016 | Cornacchia ........ A61B 18/1206 |
| 2004/0116952 | A1 * | 6/2004 | Sakurai ............. A61B 17/1628 606/169 |
| 2005/0007766 | A1 | 1/2005 | Jigamian |
| 2005/0195550 | A1 | 9/2005 | Fitzgerald et al. |
| 2006/0200120 | A1 * | 9/2006 | DiCarlo ............ A61B 18/1206 606/41 |
| 2007/0016182 | A1 | 1/2007 | Lipson et al. |
| 2007/0032789 | A1 | 2/2007 | Gonnering et al. |
| 2007/0060919 | A1 | 3/2007 | Isaacson et al. |
| 2008/0146921 | A1 * | 6/2008 | Novak ........... A61B 17/320068 600/437 |
| 2010/0262139 | A1 * | 10/2010 | Beller ............... A61B 18/1206 606/41 |
| 2011/0045680 | A1 | 2/2011 | Beller et al. |
| 2011/0178515 | A1 * | 7/2011 | Bloom ............. A61B 17/1671 606/33 |
| 2011/0276113 | A1 * | 11/2011 | Cybulski ............ A61B 18/042 607/101 |
| 2013/0274729 | A1 | 10/2013 | Orszulak |
| 2014/0142567 | A1 * | 5/2014 | Poulsen ............... A61B 18/14 606/37 |

FOREIGN PATENT DOCUMENTS

| | | |
|---|---|---|
| CN | 103156681 A | 6/2013 |
| CN | 103561672 A | 2/2014 |
| DE | 102006007828 A1 | 8/2007 |

OTHER PUBLICATIONS

Notification of First Office Action issued in corresponding Chinese application No. 20150442812.6 dated Feb. 13, 2018 with English translation, 15 pages.

Notification of Second Office Action issued in corresponding Chinese application No. 201510442812.6 dated Jul. 25, 2018 with English translation, 18 pages.

* cited by examiner

ENERGY-ACTIVATION MECHANISMS FOR SURGICAL INSTRUMENTS

CROSS REFERENCE TO RELATED APPLICATION

The present application claims the benefit of and priority to U.S. Provisional Application Ser. No. 62/042,536, filed on Aug. 27, 2014, the entire contents of which are incorporated herein by reference.

BACKGROUND

Technical Field

The present disclosure relates to energy-activation mechanisms for surgical instruments and, more particularly, to activation mechanisms for selectively initiating the supply of energy to tissue.

Background of Related Art

Various different types of surgical instruments utilize energy to treat tissue. For example, a bipolar electrosurgical forceps typically include two generally opposing electrodes charged to different electrical potentials for conducting energy therebetween and through tissue. Bipolar electrosurgical forceps utilize both mechanical clamping action and electrical energy to effect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue.

Monopolar surgical instruments, as another example, include an active electrode, and are used in conjunction with a remote return electrode, e.g., a return pad, to apply energy to tissue. Monopolar instruments have the ability to rapidly move through tissue and dissect through narrow tissue planes.

In some surgical procedures, it may be beneficial to use both bipolar and monopolar instrumentation, e.g., procedures where it is necessary to dissect through one or more layers of tissue in order to reach underlying tissue(s) to be sealed. Further, it may be beneficial, particularly with respect to endoscopic surgical procedures, to provide a single instrument incorporating both bipolar and monopolar features, thereby obviating the need to alternatingly remove and insert the bipolar and monopolar instruments in favor of one another.

Regardless of the particular configuration, energy-activation mechanisms including activation buttons and electrical switches are typically provided on the housings or handpieces of the surgical instruments to enable a surgeon to selectively initiate the supply of energy to tissue. Typically, these mechanisms are physically sealed to prevent the ingress of fluids which may trigger an errant signal that inadvertently activates the supply of energy

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

In accordance with the present disclosure, a surgical instrument is provided including a housing, an energizable member, a first activation switch, a cable assembly, and a second activation switch. The housing is operatively associated with the energizable member. The first activation switch is coupled to the energizable member and is selectively transitionable from an open condition to a closed condition. The cable assembly is coupled to the housing at a first end and includes a plug at a second, opposite end, the plug housing a second activation switch selectively transitionable from an open condition to a closed condition. The plug is adapted to connect to the source of electrosurgical energy, wherein transitioning of the first activation switch from the open condition to the closed condition transitions the second activation switch from the open condition to the closed condition such that the second activation switch communicates with the source of electrosurgical energy to initiate the supply of energy to the energizable member. The second activation switch is isolated from the first activation switch to prevent any environmental conditions affecting the surgical instrument from inadvertently communicating with the source of electrosurgical energy to initiate the supply of energy to the energizable member.

In accordance with an aspect of the present disclosure, the surgical instrument is an electrosurgical pencil.

In accordance with another aspect of the present disclosure, the surgical instrument is a surgical forceps.

In another aspect of the present disclosure, the energizable member includes a monopolar assembly.

In yet another aspect of the present disclosure, the first activation switch includes an electrical circuit, mechanical actuator, electromechanical actuator, or optical actuator.

In still another aspect of the present disclosure, the second activation switch includes an electrical circuit, mechanical actuator, electromechanical actuator, or optical actuator.

In accordance with aspects of the present disclosure, a surgical instrument is provided including a housing, an energizable member, a first activation switch, a cable assembly, and a second activation switch. The housing is operatively associated with the energizable member. The first activation switch is coupled to the energizable member and is selectively transitionable from an open condition to a closed condition to provide a first signal above a first threshold. The cable assembly is coupled to the housing at a first end and includes a plug at a second opposite end, the plug housing a second activation switch selectively transitionable from an open condition to a closed condition, the second activation switch transitioned from an open condition to the close condition upon receipt of the first signal and configured to provide a second signal above a second threshold upon closure of the second activation switch. The plug is adapted to connect to the source of electrosurgical energy such that transitioning of the second activation switch from the open condition to the closed condition position provides the second signal to the source of electrosurgical energy to initiate the supply of energy to the energizable member, wherein the second signal is above a second threshold and below the first threshold. The second activation switch is isolated from the first activation switch to prevent any environmental conditions affecting the surgical instrument from inadvertently communicating with the source of electrosurgical energy to initiate the supply of energy to the energizable member.

In an aspect of the present disclosure, the first threshold is a predetermined value sufficient to transition the second activation switch from the open condition to the closed condition.

In another aspect of the present disclosure, the predetermined value is a voltage.

In another aspect of the present disclosure, the second activation switch includes at least one transistor, the at least one transistor transitionable from the open condition to the closed condition upon receiving the predetermined voltage from the first activation switch.

In accordance with aspects of the present disclosure, a surgical instrument is provided including a housing, an energizable member, a first activation switch, a cable assembly, and a second activation switch. The housing is operatively associated with the energizable member. The first activation switch is coupled to the energizable member and is selectively transitionable from an open condition to a closed condition. The cable assembly is coupled to the housing at a first end and includes a plug at a second, opposite end, the plug housing a second activation switch selectively transitionable from an open condition to a closed condition, the second activation switch comprising a first member and a second member. The first member is movably attached to the first activation switch by a pull wire, the plug is adapted to connect to the source of electrosurgical energy such that the movement of the first activation switch from the open condition to the closed condition tensions the pull wire such that the first member moves from a first position, wherein the first member and the second member are spaced-apart from one another, to a second position, wherein the first member and the second member share a point of contact. The second activation switch transitions from an open condition to a closed condition upon the first member achieving the second position, wherein, in the closed condition, the second activation switch communicates with the source of electrosurgical energy to initiate the supply of energy to the energizable member. The second activation switch is isolated from the first activation switch to prevent any environmental conditions affecting the surgical instrument from inadvertently communicating with the source of electrosurgical energy to initiate the supply of energy to the energizable member.

In an aspect of the present disclosure, a spring is attached to the first member at a point opposite the pull wire such that the spring has a spring bias to return the first member to the first position when the first activation switch is open.

BRIEF DESCRIPTION OF THE DRAWINGS

Various aspects of the present disclosure are described herein with reference to the drawings wherein like reference numerals identify similar or identical elements:

FIG. 6A is an enlarged, cut-away view of the plug of the forceps of FIG. 6; and

DETAILED DESCRIPTION

Figure 1:
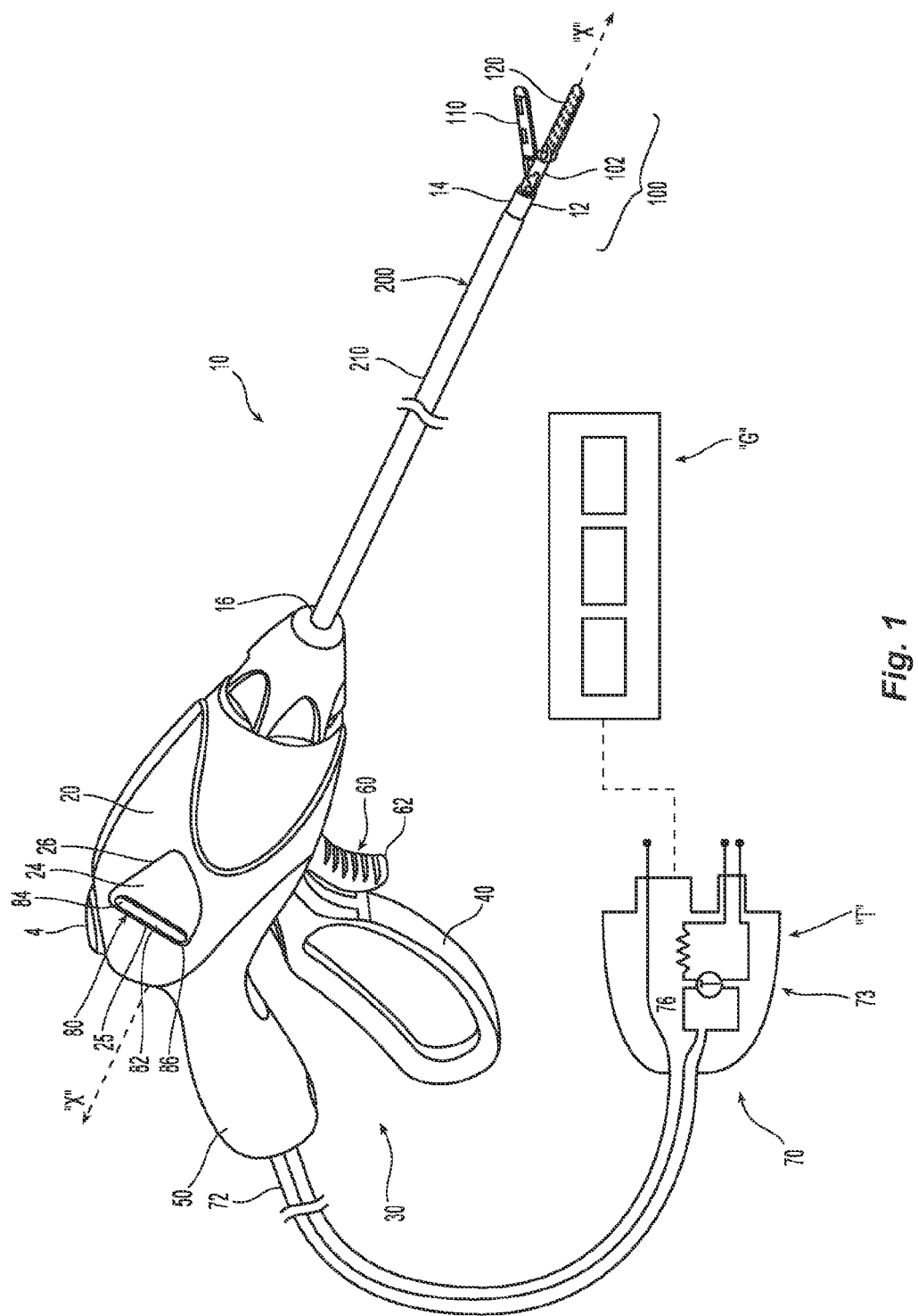
FIG. 1 is a front, perspective, partial schematic view of an endoscopic surgical forceps configured for use in accordance with the present disclosure.

Referring now to FIGS. 1-4, a forceps provided in accordance with the present disclosure is shown generally identified by reference numeral 10. Forceps 10, as will be described below, is configured to operate in both a bipolar mode, e.g., for grasping, treating, and/or dissecting tissue, and a monopolar mode, e.g., for treating and/or dissecting tissue. Although the present disclosure is shown and described with respect to forceps 10, the aspects and features of the present disclosure are equally applicable for use with any suitable surgical instrument or portion(s) thereof for actuating, moving, and/or deploying the assemblies and/or components of the surgical instrument. For example, the aspects and features of the present disclosure are equally applicable for use with an electrosurgical pencil, such as that shown in FIG. 5, or any other suitable energy-based device. Obviously, different connections and considerations apply to each particular instrument and the assemblies and/or components thereof; however, the aspects and features of the present disclosure remain generally consistent regardless of the particular instrument, assemblies, and/or components provided.

Continuing with reference to FIGS. 1-4, forceps 10 defines a longitudinal axis "X" and includes an activation button 4, a housing 20, a handle assembly 30, a trigger assembly 60, a cable assembly 70, a lever assembly 80, an end effector assembly 100, and a monopolar assembly 200. Forceps 10 further includes a shaft 12 having a distal end 14 configured to mechanically engage end effector assembly 100 and a proximal end 16 that mechanically engages housing 20. Housing 20 houses the internal working components of forceps 10.

Cable assembly 70 includes an electrosurgical cable 72 having a plug 73 at its free end for connecting forceps 10 to a generator "G" or other suitable power source, although forceps 10 may alternatively be configured as a battery powered instrument having the power and energy-generating components mounted on or within housing 20. Plug 73 is described in greater detail below. Cable 72 includes one or more wires (not shown) extending therethrough that connect to a bipolar activation switch (not shown) associated with activation button 4, and one or more wires (not shown) having sufficient length to extend through shaft 12 in order to connect to one or both of the electrically-conductive plates 112, 122 of jaw members 110, 120, respectively, for supplying energy thereto upon activation of the activation button 4 in a bipolar mode. Wires 72a, 72b of cable 72 (see FIG. 4), on the other hand, are coupled to a first activation switch 74 associated with activation button 4 and monopolar assembly 200, respectively, e.g., for supplying energy to monopolar assembly 200 upon activation of activation button 4 in a monopolar mode. As an alternative to providing a single activation button 4 associated within both the bipolar activation switch (not shown) and first activation switch 74 that initiates the supply of energy to the appropriate component(s) depending on the mode of operation of forceps 10, e.g., the bipolar mode or the monopolar mode, separate activation buttons may be provided.

Figure 2:
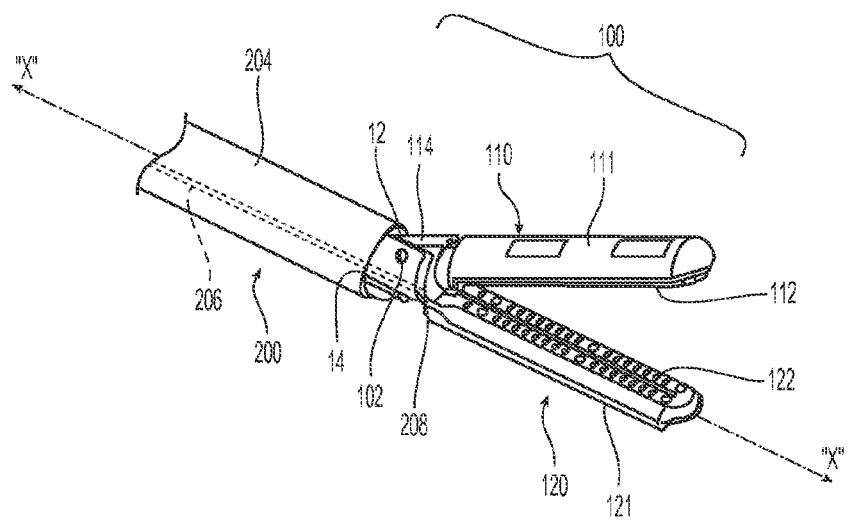
FIG. 2 is an enlarged, front, perspective view of an end effector assembly of the forceps of FIG. 1, wherein jaw members of the end effector assembly are disposed in a spaced-apart position and wherein a monopolar assembly is disposed in a retracted position.
Figure 3:
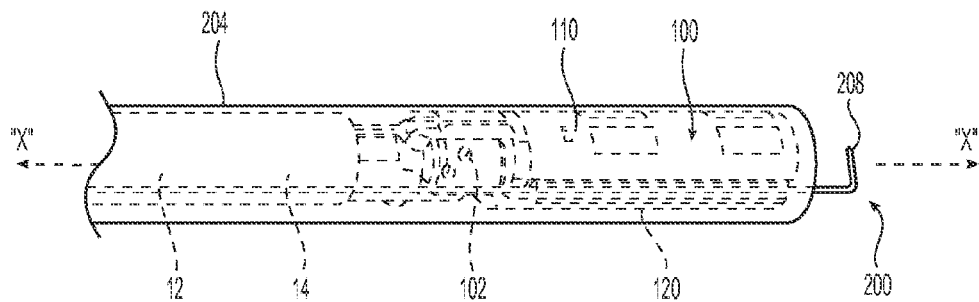
FIG. 3 is an enlarged, rear, perspective view of the end effector assembly of FIG. 2, wherein the jaw members are disposed in an approximated position and wherein the monopolar assembly is disposed in a deployed position.

Referring to FIGS. 1-3, end effector assembly 100 is shown attached at a distal end 14 of shaft 12 and includes a pair of opposing jaw members 110, 120 pivotably coupled to one another about a pivot 102. Each of the jaw members 110 and 120 includes an electrically-insulative outer jaw housing 111, 121; an electrically-conductive plate 112, 122 disposed atop respective jaw housings 111, 121; and a proximally-extending flange 114, 124, respectively (see FIG. 2). Pivot 102 extends through flanges 114, 124 to pivotably couple jaw members 110, 120 to one another. One or both of electrically-conductive plates 112, 122 are adapted to connect to a source of electrosurgical energy, such as, for example, generator "G," for conducting energy therebetween and through tissue grasped between jaw members 110, 120 to treat, e.g., seal, tissue. More specifically, in some embodiments, end effector assembly 200 defines a bipolar configuration wherein electrically-conductive plate 112 is charged to a first electrical potential and electrically-conductive plate 122 is charged to a second, different electrical potential such that an electrical potential gradient is created for conducting energy between electrically-conductive plates 112, 122 and through tissue grasped therebetween for treating e.g., sealing, tissue. Activation button 4, which is associated with an activation switch 74 coupled between generator "G" and plates 112, 122, allows the user to selectively apply energy to plates 112, 122 of end effector assembly 100 during a bipolar mode of operation. Although various activation mechanisms are detailed below with respect to activating the supply of energy to monopolar assembly 200, such activation mechanisms may similarly be configured for activating the supply of energy to electrically-conductive plates 112, 122.

Continuing with reference to FIGS. 1-3, monopolar assembly 200 includes an insulative sleeve 204 and an energizable rod member 206. Insulative sleeve 204 is slidably disposed about shaft 12 and is configured for translation about and relative to shaft 12 between a retracted position (see FIG. 2), where insulative sleeve 204 is disposed proximally of end effector assembly 100, and a deployed position (see FIG. 3), wherein insulative sleeve 204 is substantially disposed about end effector 100 so as to electrically insulate electrically-conductive plates 112, 122 of jaw members 110, 120, respectively. Energizable rod member 206 extends through sleeve 204 and distally therefrom, ultimately defining an electrically-conductive distal tip 208. Distal tip 226 may be hook-shaped (as shown), or may define any other suitable configuration, e.g., linear, ball circular, angled, etc. Energizable rod member 206 and, more specifically, distal tip 208 thereof, functions as the active electrode of monopolar assembly 200.

Sleeve 204 and rod member 206 may be fixedly engaged to one another such that sleeve 204 and rod member 206 move in concert with one another between their retracted positions (see FIG. 2), collectively the retracted position of monopolar assembly 200, and their deployed positions (see FIG. 3), collectively the deployed position of monopolar assembly 200. Insulative sleeve 204 and/or energizable rod member 206 are further coupled to lever assembly 80 such that actuation of lever assembly 80 effects corresponding deployment of insulative sleeve 204 and energizable rod member 206. Accordingly, actuation of lever 82 may be effected to move insulative sleeve 204 and energizable rod member 206 from the retracted position (see FIG. 2) to the deployed position (see FIG. 3).

Lever assembly 80 is disposed within a recess 24 defined on an exterior side surface of housing 20 (although lever assembly 80 may also be positioned at any other suitable location) and includes a lever 82 that is rotatable about a pivot 84 between a proximal position, wherein free end 86 of lever 82 is disposed at a proximal end 25 of recess 24, and a distal position, wherein free end 86 of lever 82 is disposed at a distal end 26 of recess 24. In configurations where lever assembly 80 defines a symmetrical configuration, a pair of levers 82 are provided on either side of housing 20, each of which is coupled to one end of pivot 84. Pivot 84 is rotatably coupled to housing 20 and extends through housing 20 ultimately coupling to monopolar assembly 200 via any suitable linkages, gears, etc. such that actuation of lever 82 effects deployment of monopolar assembly 200, e.g., moving of insulative sleeve 204 and energizable rod member 206 from their retracted positions (see FIG. 2) to their deployed positions (see FIG. 3).

Figure 4:
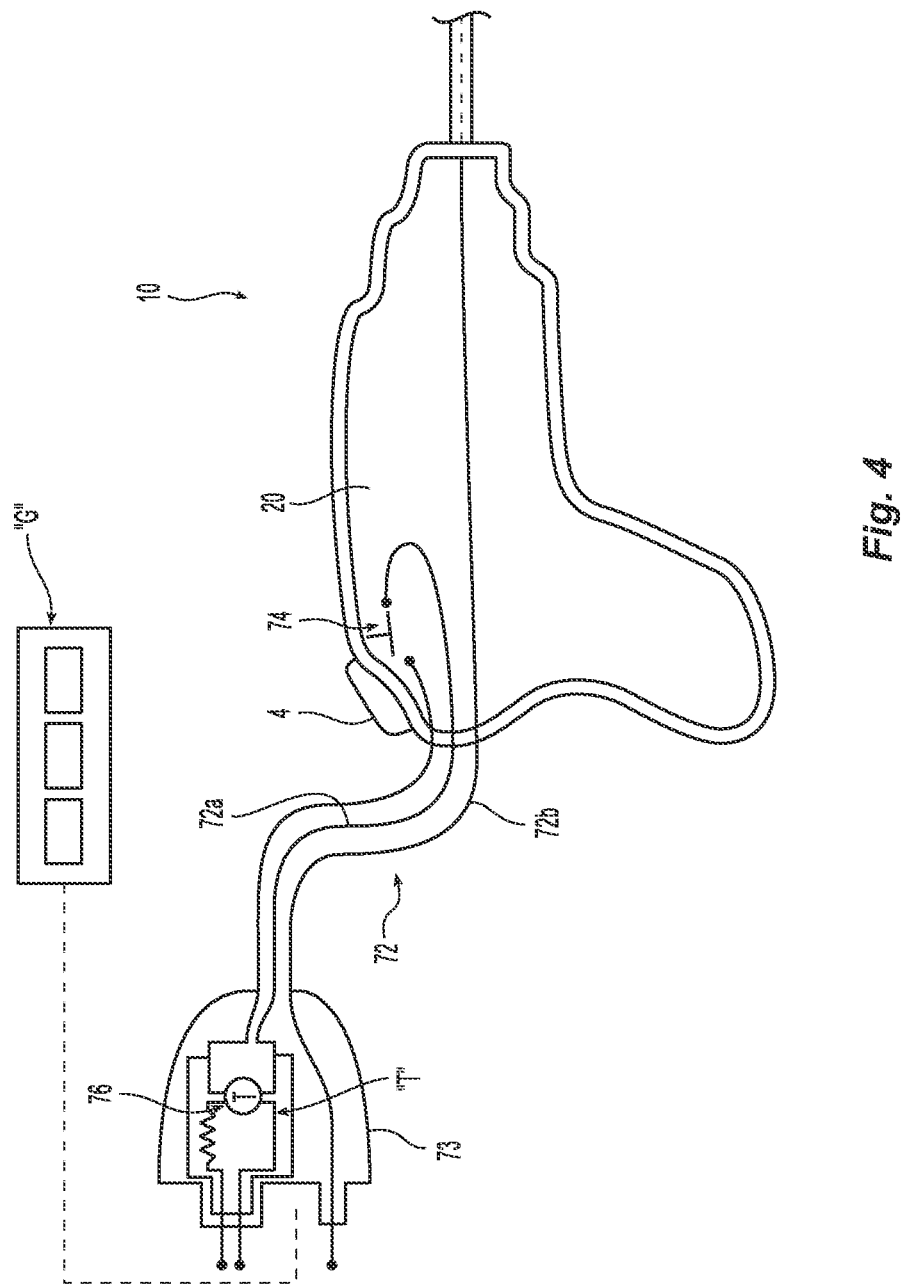
FIG. 4 is a side, cut-away, partial schematic view of the forceps of FIG. 1 showing the circuitry of the activation switch and the plug switch, wherein the internal components of the forceps have been removed for clarity purposes.

With reference to FIG. 4 in particular, wires 72a and 72b, as mentioned above, extend from electrosurgical cable 72 through housing 20 and are coupled to first activation switch 74 and energizable rod member 206, respectively, to provide energy to energizable rod member 206 (FIGS. 2 and 3) upon actuation of activation button 4. More specifically, activation button 4 is movable between a first position, corresponding to the open condition of first activation switch 74, and a second position, corresponding the closed condition of first activation switch 74. In the closed condition of first activation switch 74, there is a definite resistance R1 across the first activation switch 74. As detailed below, a second activation switch 76 is provided within plug 73 of cable assembly 70. Second activation switch 76 is transitionable from an open condition to a closed condition. In the closed condition of second activation switch 76, there is a definite resistance R2 across the second activation switch 76.

Upon closing first activation switch 74, e.g., due to the depression of activation button 4, the electrical circuit of first activation switch 74 is complete and the definite resistance R1 across activation switch 74 is established. As such, a first signal, in the form of a voltage, for example, is relayed to second activation switch 76. This first signal, or voltage, is transmitted via wires 72a and is sufficient to close second activation 76. In embodiments, second activation switch 76 is a transistor "T." In such embodiments, the voltage signal is sufficient to satisfy the voltage threshold of transistor "T," thereby closing second activation switch 76. When second activation switch 76 is closed, the electrical circuit of second activation switch 76 is closed and a definite resistance R2 across second activation switch 76 is established. As such, a second signal, in the form of a voltage, for example, is relayed to the source of electrosurgical energy "G," to which plug 73 is coupled. Upon receipt of such the second signal, the supply of energy to energizable rod member 206 (FIGS. 2 and 3) may be initiated.

It is understood that the ingress of fluids, such as, for example, blood into a switch can unwantedly close an electrical circuit. In such situations, an errant signal may be sent to the source of electrosurgical energy to energize an energizable member. To prevent this situation, switches have been physically sealed to prevent the ingress of fluids. In accordance with the present disclosure, the second activation switch is isolated from the first activation switch to prevent any environmental conditions affecting the surgical instrument from inadvertently communicating with the source of electrosurgical energy to initiate the supply of energy to the energizable member. In particular, the present disclosure uses a two-step activation process, as detailed above, to obviate the need for the physical sealing of switches. Using the two-step activation process nullifies the effects of fluid ingression into a switch, such as, for example, first activation switch 74, because in order to communicate with the source of electrosurgical energy "G," the second activation switch 76 has to also be activated. Ingress of fluids, such as blood, into first activation switch 74 may close first activation switch 74 and establish a resistance R3 across the first activation switch 74; wherein R1 is less than R3. As such, with a higher resistance R3 across first activation switch 74, the first signal, e.g., voltage, supplied from first activation switch 74 to second activation switch 76 would be insufficient to close second activation switch 76. Therefore, the first signal required to close section activation switch 74 would only be sufficient where the resistance across the first activation switch 74 is R1 or lower.

Resistance R2 may be greater than R1, such that a relatively smaller second signal, e.g., voltage, is transmitted from second activation switch 76 to the energy source "G." Such a configuration is allowable because fluid ingress is not a concern with plug 73, which is remotely positioned relative to blood and other bodily and/or surgical fluids. Further, R2 may be set equal to the resistance value of the first activation switch 74 in housing 20, such that compatibility with the energy source "G" is not a concern and/or such that settings do not need to be adjusted. Thus, the need to seal the first activation switch 74 is obviated, while the input signal to energy source "G" remains unchanged.

To better understand the two-step activation detailed above, an example embodiment is described. In this embodiment, the required output first signal S1 is a predetermined 5 volt DC signal established upon closure of first activation switch 74. Said another way, in order to overcome the first threshold, first signal S1 has to be 5 volts DC. In situations where there is an ingress of fluids in the first activation switch 74, S1 would be less than the required 5 volts DC because the resistance R3 of the fluids is greater than the resistance R1 of the first activation switch 74. Upon receipt of first signal 51 at the second activation switch 76, transistor "T" is transitioned to the closed condition, wherein the resistance R2 in the second activation switch 76 is established. Closure of second activation switch 76, in turn, outputs a second signal S2 from the second activation switch 76 (according to the resistance R2). This second signal S2 is received by the source of electrosurgical energy "G" and is sufficient to initiate the supply of energy from the source of electrosurgical energy "G" to energizable rod member 206 through wire 72b.

Figure 5:
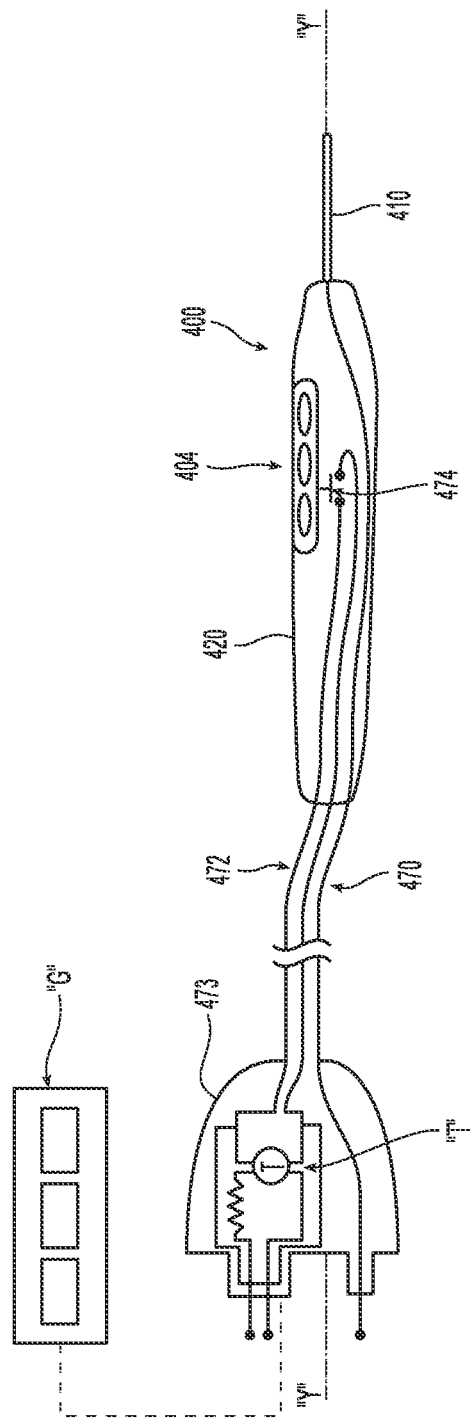
FIG. 5 is a side, cut-away, partial schematic view of an electrosurgical pencil configured for use in accordance with the present disclosure, showing the circuitry of the activation switch and the plug switch.

It is contemplated that, in one embodiment, the two-step activation process is applied to an electrosurgical pencil 400 as shown in FIG. 5. The two-step activation process applied to electrosurgical pencil 400 is similar to that of forceps 10 discussed above. Electrosurgical pencil 400 defines a longitudinal axis "Y" and includes activation buttons 404, a housing 420, a cable assembly 470, and an end effector assembly 410. Housing 420 houses the internal working components of electrosurgical pencil 400, including a first activation switch 474. Cable assembly 470 includes an electrosurgical cable 472 having a plug 473 at its free end for connecting electrosurgical pencil 400 to a generator "G" or another suitable power source. However, it is contemplated that in one embodiment, electrosurgical pencil 400 may alternatively be configured as a battery powered instrument having the power and energy-generating components on or within housing 420. Plug 473 includes a second activation switch 476. Cable 472 is coupled to a first activation switch 474 associated with activation buttons 404 and end effector assembly 410 for supplying monopolar energy upon activation of activation buttons 404.

Figure 6:
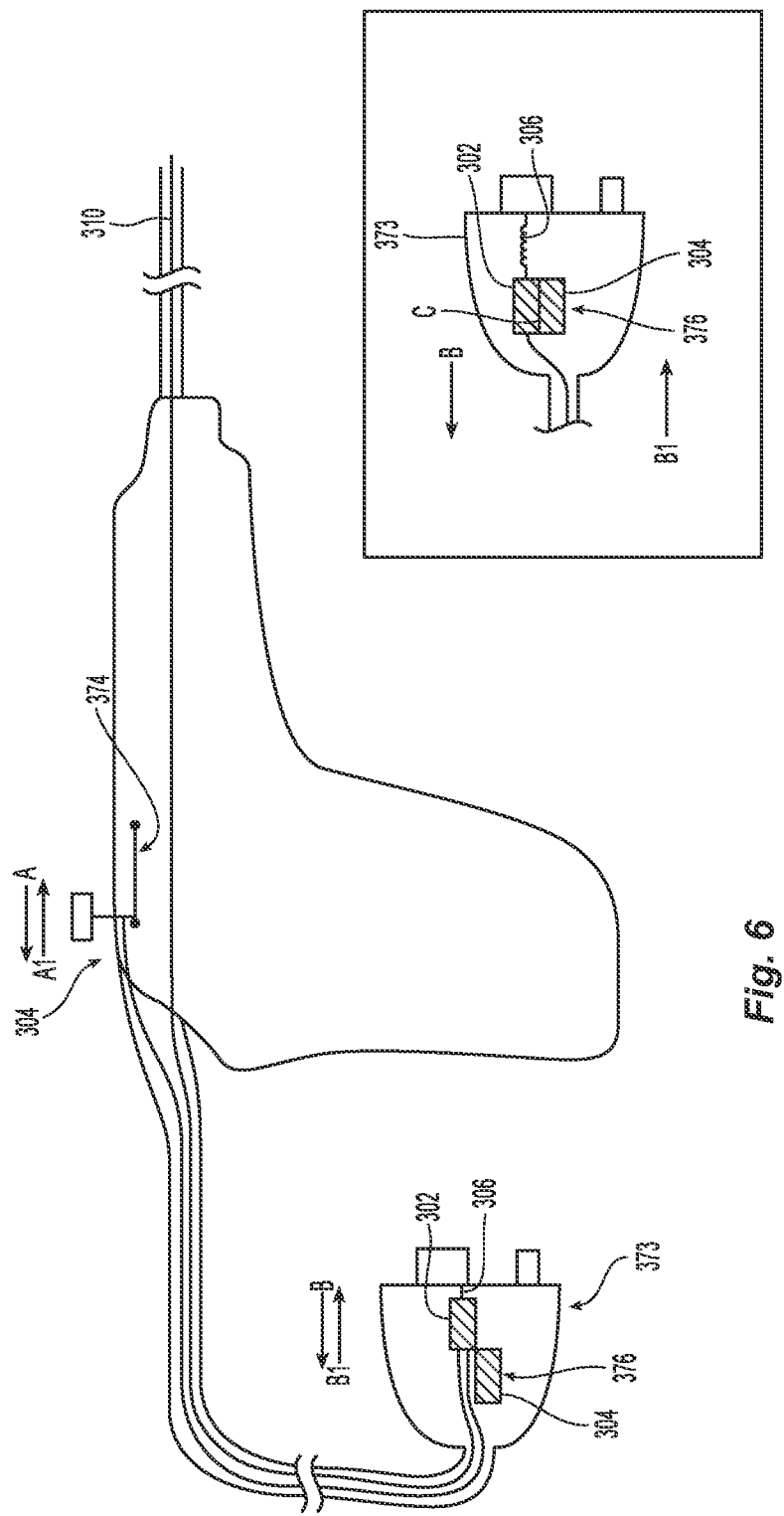
FIG. 6 is a side, cut-away view of another forceps configured for use in accordance with the present disclosure, similar to the forceps of FIG. 1, showing the configuration of the activation switch and plug switch, wherein the internal components of the forceps have been removed for clarity purposes.

The two-step activation process may be applied to forceps 300 as shown in FIG. 6. Forceps 300 is similar to forceps 10 as discussed above with the exception of activation switches 374 and 376. Continuing with reference to FIG. 6, activation switches 374, 376 may alternatively include mechanical actuators, electromechanical actuators, or optical actuators. For example, in one embodiment, first activation switch 374, similar to first activation switch 74, includes a mechanical actuator 304 where first activation switch 374 is selectively transitional from an open condition to a closed condition by moving mechanical actuator 304 from a first position to a second position as shown by arrow A1. In this embodiment, second activation switch 376 comprises a first member 302 and a second member 304. First member 302 extends longitudinally between a proximal end 302a and a distal end 302b. Proximal end 302a of first member 302 is coupled to plug 373 using a biasing member, such as, for example, spring 306. The biasing member may not be limited to a spring and may be any mechanism or component that provides a suitable bias. Distal end 302b of first member 302 is operably connected to first activation switch 374 using pull wire 308. As such, movement of first activation switch 374 from the first position to the second position according to arrow A1 tensions the pull wire 308. Under tension, the first member 302 moves in the direction of arrow B such that the first member 302 and the second member 304 share a point of contact C as shown in FIG. 6A. When the first member 302 and the second member 304 share the point of contact C, the second activation switch 376 is activated (closed) and is able to communicate with the source of electrosurgical energy "G" to provide energy to energizable member 310. When the pull wire 308 is not under tension, first member 302 is moved back to the first position given by arrow B1 by biasing member 306. In the first position, first member 302 and second member 304 do not share a point of contact C and the second activation switch 376 is not activated (remains open).

Figure 7:
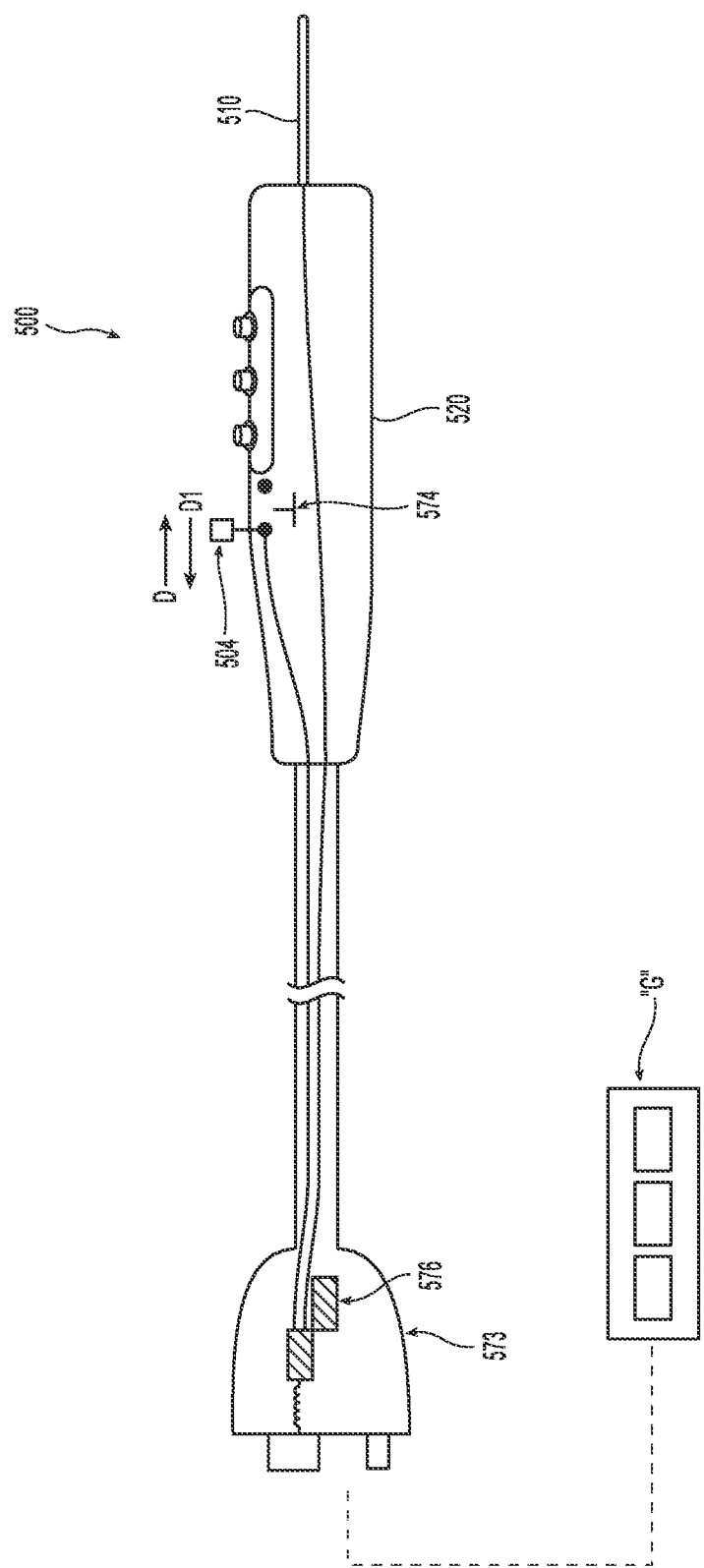
FIG. 7 is a side, cut-away view of another electrosurgical pencil configured for use in accordance with the present disclosure, similar to the pencil of FIG. 5, showing the configuration of the activation switch and plug switch, wherein the internal components of the pencil have been removed for clarity purposes.

The above-detailed embodiment of activations switches 374, 376 may likewise be applied to an electrosurgical pencil 500 as shown in FIG. 7. Electrosurgical pencil 500 is similar to electrosurgical 400 discussed above with the exception of activation switches 574 and 576, which are similar to that of forceps 300. In particular, activation switches 574 and 576 may alternatively include mechanical actuators, electromechanical actuators, or optical actuators. In one embodiment, electrosurgical pencil 500 includes a mechanical actuator 504 to selectively transition the first activation switch 574 from an open condition to a closed condition. The two-step activation process detailed with regards to activation switches 374 and 376 may likewise be applied to this embodiment.

The various embodiments disclosed herein may also be configured to work with robotic surgical systems and what is commonly referred to as "Telesurgery". Such systems employ various robotic elements to assist the surgeon in the operating theater and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include, remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely controls the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.), which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
   a housing including an energizable member coupled thereto;
   a first activation switch coupled to the energizable member and selectively transitionable from an open condition to a closed condition; and
   a cable assembly coupled to the housing at a first end and having a plug at a second, opposite end, the plug housing a second activation switch selectively transitionable from an open condition to a closed condition, the plug adapted to directly connect to a generator configured to supply electrosurgical energy, wherein transitioning of the first activation switch from the open condition to the closed condition transitions the second activation switch from the open condition to the closed condition such that the second activation switch communicates with the generator to initiate the supply of electrosurgical energy to the energizable member.

2. The surgical instrument as recited in claim 1, wherein the surgical instrument is an electrosurgical pencil.

3. The surgical instrument as recited in claim 1, wherein the surgical instrument is a surgical forceps.

4. The surgical instrument as recited in claim 1, wherein the energizable member includes a monopolar assembly.

5. The surgical instrument as recited in claim 1, wherein the first activation switch includes an electrical circuit, mechanical actuator, electromechanical actuator, or optical actuator.

6. The surgical instrument as recited in claim 1, wherein the second activation switch includes an electrical circuit, mechanical actuator, electromechanical actuator, or optical actuator.

7. A surgical instrument, comprising:
   a housing including an energizable member coupled thereto;
   a first activation switch coupled to the energizable member and selectively transitionable from an open condition to a closed condition to provide a first signal above a first threshold; and
   a cable assembly coupled to the housing at a first end and having a plug at a second, opposite end, the plug housing a second activation switch selectively transitionable from an open condition to a closed condition, the second activation switch transitions from the open condition to the closed condition upon receipt of the first signal and configured to provide a second signal above a second threshold upon closure of the second activation switch, the plug adapted to directly connect to a generator configured to supply electrosurgical energy such that transitioning of the second activation switch from the open condition to the closed condition position provides the second signal to the generator to initiate the supply of electrosurgical energy to the energizable member, wherein the second signal is above the second threshold and below the first threshold.

8. The surgical instrument as recited in claim 7, wherein the surgical instrument is an electrosurgical pencil.

9. The surgical instrument as recited in claim 7, wherein the surgical instrument is a surgical forceps.

10. The surgical instrument as recited in claim 7, wherein the first threshold is a predetermined value sufficient to transition the second activation switch from the open condition to the closed condition.

11. The surgical instrument as recited in claim 10, wherein the predetermined value is a voltage.

12. The surgical instrument as recited in claim 11, wherein the second activation switch includes at least one transistor, the at least one transistor transitionable from the open condition to the closed condition upon receiving the predetermined voltage from the first activation switch.

13. The surgical instrument as recited in claim 7, wherein the energizable member is an energizable monopolar member.

14. A surgical instrument, comprising:
   a housing having an energizable member coupled thereto;
   a first activation switch coupled to the energizable member and selectively transitionable from an open condition to a closed condition; and a cable assembly coupled to the housing at a first end and having a plug at a second, opposite end, the plug housing a second activation switch selectively transitionable from an open condition to a closed condition, the second activation switch comprising a first member and a second member, the first member movably attached to the first activation switch by a pull wire, the plug adapted to directly connect to a generator configured to supply electrosurgical energy such that the movement of the first activation switch from the open condition to the closed condition tensions the pull wire such that the first member moves from a first position, wherein the first member and the second member are spaced-apart from one another, to a second position, wherein the first member and the second member share a point of contact, the second activation switch transitioning from an open condition to a closed condition upon the first member achieving the second position, wherein, in the closed condition, the second activation switch communicates with the generator to initiate the supply of electrosurgical energy to the energizable member.

15. The surgical instrument as recited in claim 14, wherein the surgical instrument is an electrosurgical pencil.

16. The surgical instrument as recited in claim 14, wherein the surgical instrument is a surgical forceps.

17. The surgical instrument as recited in claim 14, wherein a spring is attached to the first member at a point opposite the pull wire such that the spring has a spring bias to return the first member to the first position when the first activation switch is open.

18. The surgical instrument as recited in claim 14, wherein the energizable member is an energizable monopolar member.

* * * * *